(12) United States Patent
Laufer (10) Patent No.: US 9,345,532 B2
(45) Date of Patent: May 24, 2016

(54) METHODS AND DEVICES FOR ABLATION OF TISSUE

(75) Inventor: Michael D. Laufer, Menlo Park, CA (US)

(73) Assignee: Broncus Medical Inc., San Jose, CA (US)

( * ) Notice: Subject to any disclaimer, the term of this patent is extended or adjusted under 35 U.S.C. 154(b) by 546 days.

(21) Appl. No.: 13/469,805

(22) Filed: May 11, 2012

(65) Prior Publication Data

US 2013/0046296 A1    Feb. 21, 2013

Related U.S. Application Data

(63) Continuation-in-part of application No. 13/107,720, filed on May 13, 2011, now Pat. No. 8,709,034, and a continuation-in-part of application No. 13/107,759, filed on May 13, 2011.

(60) Provisional application No. 61/486,206, filed on May 13, 2011, provisional application No. 61/485,621, filed on May 13, 2011.

(51) Int. Cl.
*A61B 18/04* (2006.01)
*A61B 18/14* (2006.01)
(Continued)

(52) U.S. Cl.
CPC . *A61B 18/14* (2013.01); *A61B 5/06* (2013.01); *A61B 18/082* (2013.01);
(Continued)

(58) Field of Classification Search
CPC .. A61B 18/14; A61B 18/082; A61B 18/1492; A61B 5/06; A61B 2018/1425; A61B 2018/00577; A61B 2018/00601; A61B 2018/1213; A61B 2019/202

USPC .................. 606/27, 32, 41, 45–50
See application file for complete search history.

(56) References Cited

U.S. PATENT DOCUMENTS 2,127,903 A    8/1938    Bowen
3,174,851 A    3/1965    Buehler et al.
(Continued)

FOREIGN PATENT DOCUMENTS

EP    0316789 A2    5/1989
EP    0347098 A2    12/1989
(Continued)

OTHER PUBLICATIONS

Choong, C., et al., "Feasibility and safety of airway bypass stent placement and influence of topical mitomycin C on stent patency," *J. Thorac. Cardiovasc Surg.*, 129:632-638, 2005.
(Continued)

*Primary Examiner* — Ashley Fishback
(74) *Attorney, Agent, or Firm* — Levine Bagade Han LLP (57) ABSTRACT

Various apparatus and methods for ablating tissue are described therein. In certain variations, a method for ablating tissue may include advancing one or more electrodes, e.g., a first electrode and a second electrode, to or near a target tissue in a subject. The electrodes may be energized such that the electrodes create a plasma arc. The plasma arc generates heat which desiccates or ablates the target tissue. An apparatus for ablating tissue may include an elongate instrument, e.g., a tube or rod. One or more electrodes, e.g., a first electrode and a second electrode, may be provided in the elongate instrument. The electrodes may be energized such that the electrodes create a plasma arc for generating heat to desiccate or ablate a target tissue.

19 Claims, 2 Drawing Sheets

(51) Int. Cl.
*A61B 18/08* (2006.01)
*A61B 18/00* (2006.01)
*A61B 18/12* (2006.01)
*A61B 19/00* (2006.01)
*A61B 5/06* (2006.01)

(52) U.S. Cl.
CPC .. *A61B 18/1492* (2013.01); *A61B 2018/00577* (2013.01); *A61B 2018/00601* (2013.01); *A61B 2018/1213* (2013.01); *A61B 2018/1425* (2013.01); *A61B 2019/202* (2013.01)

(56) References Cited

U.S. PATENT DOCUMENTS

| | | |
|---|---|---|
| 3,351,463 A | 11/1967 | Rozner et al. |
| 3,406,685 A | 10/1968 | May |
| 3,433,226 A | 3/1969 | Boyd |
| 3,556,079 A | 1/1971 | Omizo |
| 3,565,062 A | 2/1971 | Kuris |
| 3,617,060 A | 11/1971 | Lezzi |
| 3,707,151 A | 12/1972 | Jackson |
| 3,753,700 A | 8/1973 | Harrison et al. |
| 3,779,234 A | 12/1973 | Eggleton et al. |
| 3,823,717 A | 7/1974 | Pohlman et al. |
| 3,828,790 A | 8/1974 | Curtiss et al. |
| 3,874,388 A | 4/1975 | King et al. |
| 3,889,688 A | 6/1975 | Eamkaow |
| 3,942,530 A | 3/1976 | Northeved |
| 4,249,539 A | 2/1981 | Vilkomerson et al. |
| 4,249,541 A | 2/1981 | Pratt |
| 4,319,580 A | 3/1982 | Colley et al. |
| 4,324,235 A | 4/1982 | Beran |
| 4,327,739 A | 5/1982 | Chmiel et al. |
| 4,332,254 A | 6/1982 | Lundquist |
| 4,355,426 A | 10/1982 | MacGregor |
| 4,407,294 A | 10/1983 | Vilkomerson |
| 4,431,006 A | 2/1984 | Trimmer et al. |
| 4,469,142 A | 9/1984 | Harwood |
| 4,493,320 A | 1/1985 | Treat |
| 4,503,569 A | 3/1985 | Dotter |
| 4,534,761 A | 8/1985 | Raible |
| 4,538,606 A | 9/1985 | Whited |
| 4,538,618 A | 9/1985 | Rosenberg et al. |
| 4,582,067 A | 4/1986 | Silverstein et al. |
| 4,583,969 A | 4/1986 | Mortensen |
| 4,622,968 A | 11/1986 | Persson |
| 4,655,771 A | 4/1987 | Wallsten |
| 4,658,817 A | 4/1987 | Hardy |
| 4,674,498 A | 6/1987 | Stasz |
| 4,676,782 A | 6/1987 | Yamamoto et al. |
| 4,682,596 A | 7/1987 | Bales et al. |
| 4,687,482 A | 8/1987 | Hanson |
| 4,702,252 A | 10/1987 | Brooks et al. |
| 4,706,689 A | 11/1987 | Man |
| 4,750,902 A | 6/1988 | Wuchinich et al. |
| 4,753,236 A | 6/1988 | Healey |
| 4,757,821 A | 7/1988 | Snyder |
| 4,757,822 A | 7/1988 | Di Giuliomaria et al. |
| 4,767,627 A | 8/1988 | Caldwell et al. |
| 4,769,031 A | 9/1988 | McGough et al. |
| 4,770,185 A | 9/1988 | Silverstein et al. |
| 4,771,788 A | 9/1988 | Millar |
| 4,773,413 A | 9/1988 | Hussein et al. |
| 4,781,676 A | 11/1988 | Schweighardt et al. |
| 4,785,402 A | 11/1988 | Matsuo et al. |
| 4,795,465 A | 1/1989 | Marten |
| 4,802,476 A | 2/1989 | Noerenberg et al. |
| 4,807,634 A | 2/1989 | Enjoji et al. |
| 4,808,153 A | 2/1989 | Parisi |
| 4,834,102 A | 5/1989 | Schwarzchild et al. |
| 4,855,563 A | 8/1989 | Beresnev et al. |
| 4,869,268 A | 9/1989 | Yoon |
| 4,870,953 A | 10/1989 | Don Micheal et al. |
| 4,887,606 A | 12/1989 | Yock et al. |
| 4,892,098 A | 1/1990 | Sauer |
| 4,892,099 A | 1/1990 | Ohkawa et al. |
| 4,899,757 A | 2/1990 | Pope, Jr. et al. |
| 4,917,097 A | 4/1990 | Proudian et al. |
| 4,920,954 A | 5/1990 | Alliger et al. |
| 4,921,483 A | 5/1990 | Wijay et al. |
| 4,924,863 A | 5/1990 | Sterzer |
| 4,930,525 A | 6/1990 | Palestrant |
| 4,936,281 A | 6/1990 | Stasz |
| 4,955,377 A | 9/1990 | Lennox et al. |
| 4,957,508 A | 9/1990 | Kaneko et al. |
| 4,966,162 A | 10/1990 | Wang |
| 4,967,753 A | 11/1990 | Haase et al. |
| 4,973,301 A | 11/1990 | Nissenkorn |
| 4,976,690 A | 12/1990 | Solar et al. |
| 4,977,898 A | 12/1990 | Schwarzschild et al. |
| 4,991,602 A | 2/1991 | Amplatz |
| 5,002,058 A | 3/1991 | Martinelli |
| 5,030,201 A | 7/1991 | Palestrant |
| 5,042,981 A | 8/1991 | Gross |
| 5,047,026 A | 9/1991 | Rydell |
| 5,054,483 A | 10/1991 | Marten et al. |
| 5,061,275 A | 10/1991 | Wallsten et al. |
| 5,064,435 A | 11/1991 | Porter |
| 5,069,664 A | 12/1991 | Guess et al. |
| 5,081,993 A | 1/1992 | Kitney et al. |
| 5,100,423 A | 3/1992 | Fearnot |
| 5,102,417 A | 4/1992 | Palmaz |
| 5,105,816 A | 4/1992 | Shimura et al. |
| 5,105,817 A | 4/1992 | Uchibori et al. |
| 5,123,917 A | 6/1992 | Lee |
| 5,125,926 A | 6/1992 | Rudko et al. |
| 5,127,917 A | 7/1992 | Niederhauser et al. |
| 5,131,394 A | 7/1992 | Gehlbach |
| 5,145,684 A | 9/1992 | Liversidge et al. |
| 5,148,809 A | 9/1992 | Biegeleisen-Knight et al. |
| 5,155,435 A | 10/1992 | Kaufman et al. |
| 5,170,793 A | 12/1992 | Takano et al. |
| 5,178,635 A | 1/1993 | Gwon et al. |
| 5,190,528 A | 3/1993 | Fonger et al. |
| 5,201,316 A | 4/1993 | Pomeranz et al. |
| 5,201,741 A | 4/1993 | Dulebohn |
| 5,209,721 A | 5/1993 | Wilk |
| 5,220,924 A | 6/1993 | Frazin |
| 5,226,421 A | 7/1993 | Frisbie et al. |
| 5,234,447 A | 8/1993 | Kaster et al. |
| 5,238,027 A | 8/1993 | Lee |
| 5,246,011 A | 9/1993 | Caillouette |
| 5,246,014 A | 9/1993 | Williams et al. |
| 5,254,112 A | 10/1993 | Sinofsky et al. |
| 5,257,990 A | 11/1993 | Nash |
| 5,259,385 A | 11/1993 | Miller et al. |
| 5,261,409 A | 11/1993 | Dardel |
| 5,263,992 A | 11/1993 | Guire |
| 5,269,326 A | 12/1993 | Verrier |
| 5,273,529 A | 12/1993 | Idowu |
| 5,275,166 A | 1/1994 | Vaitekunas et al. |
| 5,282,799 A | 2/1994 | Rydell |
| 5,282,824 A | 2/1994 | Gianturco |
| 5,287,861 A | 2/1994 | Wilk |
| 5,295,484 A | 3/1994 | Marcus et al. |
| 5,299,578 A | 4/1994 | Rotteveel et al. |
| 5,304,200 A | 4/1994 | Spaulding |
| 5,309,915 A | 5/1994 | Ember |
| 5,311,871 A | 5/1994 | Yock |
| 5,313,950 A | 5/1994 | Ishikawa et al. |
| 5,316,001 A | 5/1994 | Ferek-Petric et al. |
| 5,318,564 A | 6/1994 | Eggers |
| 5,320,106 A | 6/1994 | Tanaka |
| 5,330,500 A | 7/1994 | Song |
| 5,334,146 A | 8/1994 | Ozasa |
| 5,334,183 A | 8/1994 | Wuchinich |
| 5,334,210 A | 8/1994 | Gianturco |
| 5,338,305 A | 8/1994 | Plyley et al. |
| 5,339,289 A | 8/1994 | Erickson |
| 5,344,420 A | 9/1994 | Hilal et al. |
| 5,351,693 A | 10/1994 | Taimisto et al. |
| 5,363,852 A | 11/1994 | Sharkawy |
| 5,363,853 A | 11/1994 | Lieber et al. |

(56) References Cited

U.S. PATENT DOCUMENTS

| | | |
|---|---|---|
| 5,366,504 A | 11/1994 | Andersen et al. |
| 5,368,035 A | 11/1994 | Hamm et al. |
| 5,372,138 A | 12/1994 | Crowley et al. |
| 5,375,602 A | 12/1994 | Lancee et al. |
| 5,377,682 A | 1/1995 | Ueno et al. |
| 5,380,316 A | 1/1995 | Aita et al. |
| 5,381,795 A | 1/1995 | Nordgren et al. |
| 5,383,460 A | 1/1995 | Jang et al. |
| 5,383,887 A | 1/1995 | Nadal |
| 5,385,148 A | 1/1995 | Lesh et al. |
| 5,389,096 A | 2/1995 | Aita et al. |
| 5,402,792 A | 4/1995 | Kimura |
| 5,409,012 A | 4/1995 | Sahatjian |
| 5,409,019 A | 4/1995 | Wilk |
| 5,411,466 A | 5/1995 | Hess |
| 5,413,601 A | 5/1995 | Keshelava |
| 5,421,955 A | 6/1995 | Lau et al. |
| 5,425,739 A | 6/1995 | Jessen |
| 5,427,107 A | 6/1995 | Milo et al. |
| 5,429,144 A | 7/1995 | Wilk |
| 5,435,314 A | 7/1995 | Dias |
| 5,441,515 A | 8/1995 | Khosravi et al. |
| 5,443,498 A | 8/1995 | Fontaine |
| 5,443,843 A | 8/1995 | Curatolo et al. |
| 5,452,733 A | 9/1995 | Sterman et al. |
| 5,454,373 A | 10/1995 | Koger et al. |
| 5,454,809 A | 10/1995 | Janssen |
| 5,456,258 A | 10/1995 | Kondo et al. |
| 5,458,120 A | 10/1995 | Lorraine |
| 5,464,016 A | 11/1995 | Nicholas et al. |
| 5,465,726 A | 11/1995 | Dickinson et al. |
| 5,466,242 A | 11/1995 | Mori |
| 5,470,308 A | 11/1995 | Edwards et al. |
| 5,474,075 A | 12/1995 | Goldberg et al. |
| 5,474,543 A | 12/1995 | McKay |
| 5,484,416 A | 1/1996 | Gittings |
| 5,485,841 A | 1/1996 | Watkin et al. |
| 5,500,012 A | 3/1996 | Brucker et al. |
| 5,505,088 A | 4/1996 | Chandraratna et al. |
| 5,509,900 A | 4/1996 | Kirkman |
| 5,514,154 A | 5/1996 | Lau et al. |
| 5,520,684 A | 5/1996 | Imran |
| 5,522,822 A | 6/1996 | Phelps et al. |
| 5,524,630 A | 6/1996 | Crowley |
| 5,527,292 A | 6/1996 | Adams et al. |
| 5,527,324 A | 6/1996 | Krantz et al. |
| 5,531,780 A | 7/1996 | Vachon |
| 5,536,240 A | 7/1996 | Edwards et al. |
| 5,540,713 A | 7/1996 | Schnepp-Pesch et al. |
| 5,545,195 A | 8/1996 | Lennox et al. |
| 5,545,208 A | 8/1996 | Wolff et al. |
| 5,545,210 A | 8/1996 | Hess et al. |
| 5,554,118 A | 9/1996 | Jang |
| 5,554,152 A | 9/1996 | Aita et al. |
| 5,554,181 A | 9/1996 | Das |
| 5,555,886 A | 9/1996 | Weng et al. |
| 5,562,922 A | 10/1996 | Lambert |
| 5,564,434 A | 10/1996 | Halperin et al. |
| 5,571,086 A | 11/1996 | Kaplan et al. |
| 5,571,180 A | 11/1996 | Blom |
| 5,573,531 A | 11/1996 | Gregory |
| 5,575,815 A | 11/1996 | Slepian et al. |
| 5,575,818 A | 11/1996 | Pinchuk |
| 5,588,432 A | 12/1996 | Crowley |
| 5,593,417 A | 1/1997 | Rhodes |
| 5,593,442 A | 1/1997 | Klein |
| 5,596,989 A | 1/1997 | Morita |
| 5,607,444 A | 3/1997 | Lam |
| 5,615,679 A | 4/1997 | Ri et al. |
| 5,616,608 A | 4/1997 | Kinsella et al. |
| 5,618,301 A | 4/1997 | Hauenstein et al. |
| 5,629,678 A | 5/1997 | Gargano et al. |
| 5,629,687 A | 5/1997 | Sutton et al. |
| 5,630,837 A | 5/1997 | Crowley |
| D380,266 S | 6/1997 | Boatman et al. |
| 5,638,819 A | 6/1997 | Manwaring et al. |
| 5,645,559 A | 7/1997 | Hachtman et al. |
| 5,647,871 A | 7/1997 | Levine et al. |
| 5,653,746 A | 8/1997 | Schmitt |
| 5,655,548 A | 8/1997 | Nelson et al. |
| 5,658,279 A | 8/1997 | Nardella et al. |
| 5,658,280 A | 8/1997 | Issa |
| 5,672,172 A | 9/1997 | Zupkas |
| 5,674,242 A | 10/1997 | Phan et al. |
| 5,674,277 A | 10/1997 | Freitag |
| 5,674,298 A | 10/1997 | Levy et al. |
| 5,678,555 A | 10/1997 | O'Connell |
| 5,682,880 A | 11/1997 | Brain |
| 5,693,085 A | 12/1997 | Buirge et al. |
| 5,702,418 A | 12/1997 | Ravenscroft |
| 5,704,361 A | 1/1998 | Seward et al. |
| 5,713,949 A | 2/1998 | Jayaraman |
| 5,716,393 A | 2/1998 | Lindenberg et al. |
| 5,718,701 A | 2/1998 | Shai et al. |
| 5,720,735 A | 2/1998 | Dorros |
| 5,725,521 A | 3/1998 | Mueller |
| 5,725,547 A | 3/1998 | Chuter |
| 5,725,572 A | 3/1998 | Lam et al. |
| 5,728,068 A | 3/1998 | Leone et al. |
| 5,733,301 A | 3/1998 | Forman |
| 5,736,642 A | 4/1998 | Yost et al. |
| 5,741,234 A | 4/1998 | Aboul-Hosn |
| 5,741,333 A | 4/1998 | Frid |
| 5,746,767 A | 5/1998 | Smith |
| 5,752,518 A | 5/1998 | McGee et al. |
| 5,755,769 A | 5/1998 | Richard et al. |
| 5,755,778 A | 5/1998 | Kleshinski |
| 5,759,174 A | 6/1998 | Fischell et al. |
| 5,759,769 A | 6/1998 | Sia et al. |
| 5,762,638 A | 6/1998 | Shikani et al. |
| 5,779,642 A | 7/1998 | Nightengale |
| 5,782,762 A | 7/1998 | Vining |
| 5,792,119 A | 8/1998 | Marx |
| 5,795,325 A | 8/1998 | Valley et al. |
| 5,797,920 A | 8/1998 | Kim |
| 5,807,261 A | 9/1998 | Benaron et al. |
| 5,810,008 A | 9/1998 | Dekel et al. |
| 5,810,836 A | 9/1998 | Hussein et al. |
| 5,819,723 A | 10/1998 | Joseph |
| 5,824,046 A | 10/1998 | Smith et al. |
| 5,824,048 A | 10/1998 | Tuch |
| 5,830,191 A | 11/1998 | Hildwein et al. |
| 5,830,222 A | 11/1998 | Makower |
| 5,840,431 A | 11/1998 | Kall |
| 5,843,079 A | 12/1998 | Suslov |
| 5,843,158 A | 12/1998 | Lenker et al. |
| 5,843,175 A | 12/1998 | Frantzen |
| 5,846,205 A | 12/1998 | Curley et al. |
| 5,849,037 A | 12/1998 | Frid |
| 5,851,210 A | 12/1998 | Torossian |
| 5,855,597 A | 1/1999 | Jayaraman |
| 5,855,598 A | 1/1999 | Pinchuk |
| 5,860,920 A | 1/1999 | McGee et al. |
| 5,860,951 A | 1/1999 | Eggers et al. |
| 5,868,763 A | 2/1999 | Spence et al. |
| 5,868,777 A | 2/1999 | Lam |
| 5,873,904 A | 2/1999 | Ragheb et al. |
| 5,876,345 A | 3/1999 | Eaton et al. |
| 5,876,434 A | 3/1999 | Flomenblit et al. |
| 5,876,445 A | 3/1999 | Andersen et al. |
| 5,876,448 A | 3/1999 | Thompson et al. |
| 5,885,219 A | 3/1999 | Nightengale |
| 5,906,587 A | 5/1999 | Zimmon |
| 5,906,621 A | 5/1999 | Secrest et al. |
| 5,908,448 A | 6/1999 | Roberts et al. |
| 5,911,702 A | 6/1999 | Romley et al. |
| 5,916,158 A | 6/1999 | Webster, Jr. |
| 5,919,191 A | 7/1999 | Lennox et al. |
| 5,922,019 A | 7/1999 | Hankh et al. |
| 5,935,135 A | 8/1999 | Bramfitt et al. |
| 5,938,697 A | 8/1999 | Killion et al. |
| 5,951,567 A | 9/1999 | Javier, Jr. et al. |
| 5,954,636 A | 9/1999 | Schwartz et al. |
| 5,954,649 A | 9/1999 | Chia et al. |

(56) References Cited

U.S. PATENT DOCUMENTS

| | | |
|---|---|---|
| 5,957,849 A | 9/1999 | Munro |
| 5,957,919 A | 9/1999 | Laufer |
| 5,957,949 A | 9/1999 | Leonhardt et al. |
| 5,957,974 A | 9/1999 | Thompson et al. |
| 5,967,990 A | 10/1999 | Thierman et al. |
| 5,968,053 A | 10/1999 | Revelas |
| 5,968,070 A | 10/1999 | Bley et al. |
| 5,971,767 A | 10/1999 | Kaufman et al. |
| 5,971,980 A | 10/1999 | Sherman |
| 5,972,017 A | 10/1999 | Berg et al. |
| 5,976,178 A | 11/1999 | Goldsteen et al. |
| 5,984,871 A | 11/1999 | TenHoff et al. |
| 5,989,276 A | 11/1999 | Houser et al. |
| 5,993,484 A | 11/1999 | Shmulewitz |
| 6,001,124 A | 12/1999 | Bachinski |
| 6,002,955 A | 12/1999 | Willems et al. |
| 6,003,517 A | 12/1999 | Sheffield et al. |
| 6,004,269 A | 12/1999 | Crowley et al. |
| 6,004,273 A | 12/1999 | Sakamoto et al. |
| 6,004,319 A | 12/1999 | Goble et al. |
| 6,007,544 A | 12/1999 | Kim |
| 6,007,546 A | 12/1999 | Snow et al. |
| 6,007,574 A | 12/1999 | Pulnev et al. |
| 6,010,529 A | 1/2000 | Herweck et al. |
| 6,011,995 A | 1/2000 | Guglielmi et al. |
| 6,013,033 A | 1/2000 | Berger et al. |
| 6,013,093 A | 1/2000 | Nott et al. |
| 6,013,854 A | 1/2000 | Moriuchi |
| 6,015,405 A | 1/2000 | Schwartz et al. |
| 6,015,415 A | 1/2000 | Avelianet |
| 6,019,787 A | 2/2000 | Richard et al. |
| 6,019,789 A | 2/2000 | Dinh et al. |
| 6,022,371 A | 2/2000 | Killion |
| 6,024,703 A | 2/2000 | Zanelli et al. |
| 6,024,756 A | 2/2000 | Huebsch et al. |
| 6,030,392 A | 2/2000 | Dakov |
| 6,032,674 A | 3/2000 | Eggers et al. |
| 6,036,702 A | 3/2000 | Bachinski et al. |
| 6,045,511 A | 4/2000 | Ott et al. |
| 6,045,532 A | 4/2000 | Eggers et al. |
| 6,048,362 A | 4/2000 | Berg |
| 6,053,940 A | 4/2000 | Wijay |
| 6,053,941 A | 4/2000 | Lindenberg et al. |
| 6,059,731 A | 5/2000 | Seward et al. |
| 6,059,811 A | 5/2000 | Pinchasik et al. |
| 6,063,111 A | 5/2000 | Hieshima et al. |
| 6,064,902 A | 5/2000 | Haissaguerre et al. |
| 6,066,169 A | 5/2000 | McGuinness |
| 6,068,638 A | 5/2000 | Makower |
| 6,070,094 A | 5/2000 | Swanson et al. |
| 6,074,349 A | 6/2000 | Crowley |
| 6,074,362 A | 6/2000 | Jang et al. |
| 6,074,416 A | 6/2000 | Berg et al. |
| 6,080,109 A | 6/2000 | Baker et al. |
| 6,080,182 A | 6/2000 | Shaw et al. |
| 6,083,162 A | 7/2000 | Vining |
| 6,093,195 A | 7/2000 | Ouchi |
| 6,096,053 A | 8/2000 | Bates |
| 6,099,563 A | 8/2000 | Zhong |
| 6,102,887 A | 8/2000 | Altman |
| 6,112,123 A | 8/2000 | Kelleher et al. |
| 6,113,612 A | 9/2000 | Swanson et al. |
| 6,117,101 A | 9/2000 | Diederich et al. |
| 6,120,432 A | 9/2000 | Sullivan et al. |
| 6,120,534 A | 9/2000 | Ruiz |
| 6,120,803 A | 9/2000 | Wong et al. |
| 6,124,523 A | 9/2000 | Banas et al. |
| 6,129,726 A | 10/2000 | Edwards et al. |
| 6,135,997 A | 10/2000 | Laufer et al. |
| 6,143,019 A | 11/2000 | Motamedi et al. |
| 6,152,937 A | 11/2000 | Peterson et al. |
| 6,152,945 A | 11/2000 | Bachinski et al. |
| 6,159,225 A | 12/2000 | Makower |
| 6,162,245 A | 12/2000 | Jayaraman |
| 6,165,127 A | 12/2000 | Crowley |
| 6,174,323 B1 | 1/2001 | Biggs et al. |
| 6,176,872 B1 | 1/2001 | Miksza |
| 6,181,348 B1 | 1/2001 | Geiger |
| 6,183,444 B1 | 2/2001 | Glines et al. |
| 6,186,942 B1 | 2/2001 | Sullivan et al. |
| 6,188,355 B1 | 2/2001 | Gilboa |
| 6,190,353 B1 | 2/2001 | Makower et al. |
| 6,197,042 B1 | 3/2001 | Ginn et al. |
| 6,200,313 B1 | 3/2001 | Abe et al. |
| 6,200,564 B1 | 3/2001 | Lamont et al. |
| 6,206,831 B1 | 3/2001 | Suorsa et al. |
| 6,226,543 B1 | 5/2001 | Gilboa et al. |
| 6,231,587 B1 | 5/2001 | Makower |
| 6,235,024 B1 | 5/2001 | Tu |
| 6,235,054 B1 | 5/2001 | Berg et al. |
| 6,239,705 B1 | 5/2001 | Glen |
| 6,241,742 B1 | 6/2001 | Spence et al. |
| 6,241,746 B1 | 6/2001 | Bosma et al. |
| 6,245,020 B1 | 6/2001 | Moore et al. |
| 6,245,057 B1 | 6/2001 | Sieben et al. |
| 6,245,102 B1 | 6/2001 | Jayaraman |
| 6,246,784 B1 | 6/2001 | Summers et al. |
| 6,254,632 B1 | 7/2001 | Wu et al. |
| 6,258,100 B1 | 7/2001 | Alferness et al. |
| 6,258,115 B1 | 7/2001 | Dubrul |
| 6,261,601 B1 | 7/2001 | Talwar et al. |
| 6,264,690 B1 | 7/2001 | Von Oepen |
| 6,270,515 B1 | 8/2001 | Linden et al. |
| 6,270,524 B1 | 8/2001 | Kim |
| 6,272,366 B1 | 8/2001 | Vining |
| 6,273,907 B1 | 8/2001 | Laufer |
| 6,280,457 B1 | 8/2001 | Wallace et al. |
| 6,283,951 B1 | 9/2001 | Flaherty et al. |
| 6,283,983 B1 | 9/2001 | Makower et al. |
| 6,283,988 B1 | 9/2001 | Laufer et al. |
| 6,287,290 B1 | 9/2001 | Perkins et al. |
| 6,290,728 B1 | 9/2001 | Phelps et al. |
| 6,292,494 B1 | 9/2001 | Baker et al. |
| 6,293,951 B1 | 9/2001 | Alferness et al. |
| 6,299,604 B1 | 10/2001 | Ragheb et al. |
| 6,299,635 B1 | 10/2001 | Frantzen |
| 6,306,096 B1 | 10/2001 | Seward et al. |
| 6,306,097 B1 | 10/2001 | Park et al. |
| 6,309,375 B1 | 10/2001 | Glines et al. |
| 6,309,415 B1 | 10/2001 | Pulnev et al. |
| 6,309,416 B1 | 10/2001 | Swanson et al. |
| 6,325,825 B1 | 12/2001 | Kula et al. |
| 6,328,689 B1 | 12/2001 | Gonzalez et al. |
| 6,331,116 B1 | 12/2001 | Kaufman et al. |
| 6,334,869 B1 | 1/2002 | Leonhardt et al. |
| 6,335,029 B1 | 1/2002 | Kamath et al. |
| 6,336,933 B1 | 1/2002 | Parodi |
| 6,342,591 B1 | 1/2002 | Zamora et al. |
| 6,343,936 B1 | 2/2002 | Kaufman et al. |
| 6,344,053 B1 | 2/2002 | Boneau |
| 6,346,940 B1 | 2/2002 | Fukunaga |
| 6,355,057 B1 | 3/2002 | DeMarais et al. |
| 6,371,964 B1 | 4/2002 | Vargas et al. |
| 6,379,382 B1 | 4/2002 | Yang |
| 6,380,732 B1 | 4/2002 | Gilboa |
| 6,391,036 B1 | 5/2002 | Berg et al. |
| 6,394,093 B1 | 5/2002 | Lethi |
| 6,394,956 B1 | 5/2002 | Chandrasekaran et al. |
| 6,409,686 B1 | 6/2002 | Guthrie et al. |
| 6,411,852 B1 | 6/2002 | Danek et al. |
| 6,428,550 B1 | 8/2002 | Vargas et al. |
| 6,440,163 B1 | 8/2002 | Swanson et al. |
| 6,451,048 B1 | 9/2002 | Berg et al. |
| 6,458,153 B1 | 10/2002 | Bailey et al. |
| 6,466,687 B1 | 10/2002 | Uppaluri et al. |
| 6,488,673 B1 | 12/2002 | Laufer et al. |
| 6,490,474 B1 | 12/2002 | Willis et al. |
| 6,493,589 B1 | 12/2002 | Medhkour et al. |
| 6,505,065 B1 | 1/2003 | Yanof et al. |
| 6,506,408 B1 | 1/2003 | Palasis |
| 6,508,822 B1 | 1/2003 | Peterson et al. |
| 6,511,491 B2 | 1/2003 | Grudem et al. |
| 6,514,249 B1 | 2/2003 | Maguire et al. |
| 6,514,290 B1 | 2/2003 | Loomas |

(56) References Cited

U.S. PATENT DOCUMENTS

| | | |
|---|---|---|
| 6,516,213 B1 | 2/2003 | Nevo |
| 6,528,301 B1 | 3/2003 | Breme et al. |
| 6,533,812 B2 | 3/2003 | Swanson et al. |
| 6,551,302 B1 | 4/2003 | Rosinko et al. |
| 6,554,848 B2 | 4/2003 | Boylan et al. |
| 6,556,696 B1 | 4/2003 | Summers et al. |
| 6,558,333 B2 | 5/2003 | Gilboa et al. |
| 6,574,498 B1 | 6/2003 | Gilboa |
| 6,575,969 B1 | 6/2003 | Rittman et al. |
| 6,585,655 B2 | 7/2003 | Crowley |
| 6,593,884 B1 | 7/2003 | Gilboa et al. |
| 6,599,303 B1 | 7/2003 | Peterson et al. |
| 6,599,311 B1 | 7/2003 | Biggs et al. |
| 6,602,263 B1 | 8/2003 | Swanson et al. |
| 6,615,155 B2 | 9/2003 | Gilboa |
| 6,616,675 B1 | 9/2003 | Evard et al. |
| 6,620,176 B1 | 9/2003 | Peterson et al. |
| 6,623,437 B2 | 9/2003 | Hinchliffe et al. |
| 6,623,448 B2 | 9/2003 | Slater |
| 6,629,951 B2 | 10/2003 | Laufer et al. |
| 6,634,363 B1 | 10/2003 | Danek et al. |
| 6,635,279 B2 | 10/2003 | Kolter et al. |
| 6,635,281 B2 | 10/2003 | Wong et al. |
| 6,650,923 B1 | 11/2003 | Lesh et al. |
| 6,652,577 B2 | 11/2003 | Gianotti |
| 6,652,582 B1 | 11/2003 | Stinson |
| 6,660,015 B1 | 12/2003 | Berg et al. |
| 6,663,662 B2 | 12/2003 | Pacetti et al. |
| 6,667,051 B1 | 12/2003 | Gregory |
| 6,673,084 B1 | 1/2004 | Peterson et al. |
| 6,689,803 B2 | 2/2004 | Hunter |
| 6,692,494 B1 | 2/2004 | Cooper et al. |
| 6,694,163 B1 | 2/2004 | Vining |
| 6,695,859 B1 | 2/2004 | Golden et al. |
| 6,699,256 B1 | 3/2004 | Logan et al. |
| 6,702,780 B1 | 3/2004 | Gilboa et al. |
| 6,702,829 B2 | 3/2004 | Bachinski et al. |
| 6,711,429 B1 | 3/2004 | Gilboa et al. |
| 6,712,804 B2 | 3/2004 | Roue et al. |
| 6,712,812 B2 | 3/2004 | Roschak et al. |
| 6,712,845 B2 | 3/2004 | Hossainy |
| 6,719,698 B2 | 4/2004 | Manor et al. |
| 6,719,781 B1 | 4/2004 | Kim |
| 6,730,064 B2 | 5/2004 | Ragheb et al. |
| 6,730,349 B2 | 5/2004 | Schwarz et al. |
| 6,749,576 B2 | 6/2004 | Bauer |
| 6,749,606 B2 | 6/2004 | Keast et al. |
| 6,770,070 B1 | 8/2004 | Balbierz |
| 6,773,457 B2 | 8/2004 | Ivancev et al. |
| 6,785,410 B2 | 8/2004 | Vining et al. |
| 6,790,228 B2 | 9/2004 | Hossainy et al. |
| 6,819,785 B1 | 11/2004 | Vining et al. |
| 6,829,379 B1 | 12/2004 | Knoplioch et al. |
| 6,833,814 B2 | 12/2004 | Gilboa et al. |
| 6,852,111 B1 | 2/2005 | Lieber |
| 6,866,674 B2 | 3/2005 | Galdonik et al. |
| 6,869,443 B2 | 3/2005 | Buscemi et al. |
| 6,872,183 B2 | 3/2005 | Sampson et al. |
| 6,886,558 B2 | 5/2005 | Tanaka |
| 6,890,583 B2 | 5/2005 | Chudzik et al. |
| 6,899,731 B2 | 5/2005 | Li et al. |
| 6,909,913 B2 | 6/2005 | Vining |
| 6,918,869 B2 | 7/2005 | Shaw et al. |
| 6,918,927 B2 | 7/2005 | Bates et al. |
| 6,920,882 B2 | 7/2005 | Berg et al. |
| 6,929,637 B2 | 8/2005 | Gonzalez et al. |
| 6,941,950 B2 | 9/2005 | Wilson et al. |
| 6,960,219 B2 | 11/2005 | Grudem et al. |
| 6,961,600 B2 | 11/2005 | Kohl et al. |
| 6,970,733 B2 | 11/2005 | Willis et al. |
| 6,994,713 B2 | 2/2006 | Berg et al. |
| 6,996,430 B1 | 2/2006 | Gilboa et al. |
| 6,997,189 B2 | 2/2006 | Biggs et al. |
| 7,011,094 B2 | 3/2006 | Rapacki et al. |
| 7,014,654 B2 | 3/2006 | Welsh et al. |
| 7,022,088 B2 | 4/2006 | Keast et al. |
| 7,052,501 B2 | 5/2006 | McGuckin |
| 7,086,398 B2 | 8/2006 | Tanaka |
| 7,149,564 B2 | 12/2006 | Vining et al. |
| 7,169,164 B2 | 1/2007 | Borillo et al. |
| 7,175,644 B2 | 2/2007 | Cooper et al. |
| 7,179,220 B2 | 2/2007 | Kukuk |
| 7,191,101 B2 | 3/2007 | Knoplioch et al. |
| 7,226,442 B2 | 6/2007 | Sheppard, Jr. et al. |
| 7,226,472 B2 | 6/2007 | Pederson, Jr. et al. |
| 7,232,409 B2 | 6/2007 | Hale et al. |
| 7,236,620 B1 | 6/2007 | Gurcan |
| 7,260,250 B2 | 8/2007 | Summers et al. |
| 7,356,367 B2 | 4/2008 | Liang et al. |
| 7,422,563 B2 | 9/2008 | Roshak et al. |
| 7,481,775 B2 | 1/2009 | Weikel et al. |
| 7,483,755 B2 | 1/2009 | Ingle et al. |
| 7,517,320 B2 | 4/2009 | Wibowo et al. |
| 7,815,590 B2 | 10/2010 | Cooper |
| 7,963,925 B1 | 6/2011 | Schecter |
| 7,985,187 B2 | 7/2011 | Wibowo et al. |
| 8,235,908 B2 | 8/2012 | Roshak et al. |
| 8,308,682 B2 | 11/2012 | Kramer et al. |
| 8,337,516 B2 | 12/2012 | Escudero et al. |
| 8,409,167 B2 | 4/2013 | Roschak |
| 8,784,400 B2 | 7/2014 | Roschak |
| 2001/0007940 A1 | 7/2001 | Tu et al. |
| 2001/0021872 A1 | 9/2001 | Bailey et al. |
| 2001/0026666 A1 | 10/2001 | Ferrera et al. |
| 2001/0027339 A1 | 10/2001 | Boatman |
| 2001/0027341 A1 | 10/2001 | Gianotti |
| 2001/0044576 A1 | 11/2001 | Vining |
| 2001/0044650 A1 | 11/2001 | Simso et al. |
| 2001/0047180 A1 | 11/2001 | Grudem et al. |
| 2001/0052344 A1 | 12/2001 | Doshi |
| 2002/0002401 A1 | 1/2002 | McGuckin et al. |
| 2002/0022833 A1 | 2/2002 | Maguire et al. |
| 2002/0028006 A1 | 3/2002 | Novak et al. |
| 2002/0028008 A1 | 3/2002 | Fan et al. |
| 2002/0032477 A1 | 3/2002 | Helmus et al. |
| 2002/0042564 A1 | 4/2002 | Cooper et al. |
| 2002/0042565 A1 | 4/2002 | Cooper et al. |
| 2002/0042622 A1 | 4/2002 | Vargas et al. |
| 2002/0049370 A1 | 4/2002 | Laufer et al. |
| 2002/0055772 A1 | 5/2002 | McGuckin et al. |
| 2002/0071902 A1 | 6/2002 | Ding et al. |
| 2002/0087153 A1 | 7/2002 | Roschak et al. |
| 2002/0091433 A1 | 7/2002 | Ding et al. |
| 2002/0111619 A1 | 8/2002 | Keast et al. |
| 2002/0111620 A1 | 8/2002 | Cooper et al. |
| 2002/0119178 A1 | 8/2002 | Levesque et al. |
| 2002/0123786 A1 | 9/2002 | Gittings et al. |
| 2002/0128647 A1 | 9/2002 | Roschak et al. |
| 2002/0131625 A1 | 9/2002 | Vining et al. |
| 2002/0133057 A1 | 9/2002 | Kukuk |
| 2002/0138074 A1 | 9/2002 | Keast et al. |
| 2002/0147462 A1 | 10/2002 | Mair et al. |
| 2002/0161321 A1 | 10/2002 | Sweezer et al. |
| 2002/0161377 A1 | 10/2002 | Rabkin |
| 2003/0017150 A1 | 1/2003 | Torphy |
| 2003/0070676 A1 | 4/2003 | Cooper et al. |
| 2003/0070682 A1 | 4/2003 | Wilson et al. |
| 2003/0120292 A1 | 6/2003 | Park et al. |
| 2003/0130657 A1 | 7/2003 | Tom et al. |
| 2003/0153971 A1 | 8/2003 | Chandrasekaran |
| 2003/0204138 A1 | 10/2003 | Choi |
| 2003/0216806 A1 | 11/2003 | Togawa et al. |
| 2004/0055606 A1 | 3/2004 | Hendricksen et al. |
| 2004/0060563 A1 | 4/2004 | Rapacki et al. |
| 2004/0073155 A1 | 4/2004 | Laufer et al. |
| 2004/0073201 A1 | 4/2004 | Cooper et al. |
| 2004/0073284 A1 | 4/2004 | Bates et al. |
| 2004/0078054 A1 | 4/2004 | Biggs et al. |
| 2004/0093070 A1 | 5/2004 | Hojeibane et al. |
| 2004/0211434 A1 | 10/2004 | Loomas et al. |
| 2004/0220496 A1 | 11/2004 | Gonzalez |
| 2004/0220556 A1 | 11/2004 | Cooper et al. |
| 2004/0261203 A1 | 12/2004 | Dworzan |
| 2005/0016530 A1 | 1/2005 | McCutcheon et al. |

(56) References Cited

U.S. PATENT DOCUMENTS

| | | |
|---|---|---|
| 2005/0043751 A1 | 2/2005 | Phan et al. |
| 2005/0043752 A1 | 2/2005 | Phan et al. |
| 2005/0049615 A1 | 3/2005 | Cooper et al. |
| 2005/0056292 A1 | 3/2005 | Cooper |
| 2005/0060041 A1 | 3/2005 | Phan et al. |
| 2005/0060042 A1 | 3/2005 | Phan et al. |
| 2005/0060044 A1 | 3/2005 | Roschak et al. |
| 2005/0085801 A1 | 4/2005 | Cooper et al. |
| 2005/0096529 A1 | 5/2005 | Cooper et al. |
| 2005/0107783 A1 | 5/2005 | Tom et al. |
| 2005/0135662 A1 | 6/2005 | Vining et al. |
| 2005/0137518 A1 | 6/2005 | Biggs et al. |
| 2005/0137611 A1 | 6/2005 | Escudero et al. |
| 2005/0137712 A1 | 6/2005 | Biggs et al. |
| 2005/0137715 A1 | 6/2005 | Phan et al. |
| 2005/0147284 A1 | 7/2005 | Vining et al. |
| 2005/0165342 A1 | 7/2005 | Odland |
| 2005/0171527 A1 | 8/2005 | Bhola |
| 2005/0177144 A1 | 8/2005 | Phan et al. |
| 2005/0182295 A1 | 8/2005 | Soper et al. |
| 2005/0182475 A1 | 8/2005 | Jen et al. |
| 2005/0192526 A1 | 9/2005 | Biggs et al. |
| 2005/0228268 A1 | 10/2005 | Cole |
| 2005/0251202 A1 | 11/2005 | Ewers et al. |
| 2005/0261550 A1 | 11/2005 | Akimoto et al. |
| 2005/0288549 A1 | 12/2005 | Mathis |
| 2006/0023966 A1 | 2/2006 | Vining |
| 2006/0116749 A1 | 6/2006 | Willink et al. |
| 2006/0135984 A1 | 6/2006 | Kramer et al. |
| 2006/0142672 A1 | 6/2006 | Keast et al. |
| 2006/0183973 A1 | 8/2006 | Kamrava |
| 2006/0254600 A1 | 11/2006 | Danek et al. |
| 2006/0276807 A1 | 12/2006 | Keast et al. |
| 2006/0280772 A1 | 12/2006 | Roschak et al. |
| 2006/0280773 A1 | 12/2006 | Roschak et al. |
| 2007/0010438 A1 | 1/2007 | Mayo et al. |
| 2007/0016072 A1 | 1/2007 | Grunwald et al. |
| 2007/0092864 A1 | 4/2007 | Reinhardt et al. |
| 2007/0123922 A1 | 5/2007 | Cooper et al. |
| 2007/0250070 A1 | 10/2007 | Nobis et al. |
| 2007/0255304 A1 | 11/2007 | Roschak et al. |
| 2008/0009760 A1 | 1/2008 | Wibowo et al. |
| 2008/0027273 A1 | 1/2008 | Gutterman |
| 2008/0039715 A1 | 2/2008 | Wilson et al. |
| 2008/0086107 A1 | 4/2008 | Roschak |
| 2008/0097139 A1 | 4/2008 | Clerk et al. |
| 2008/0213337 A1 | 9/2008 | Hermansson et al. |
| 2008/0302359 A1 | 12/2008 | Loomas et al. |
| 2008/0312543 A1 | 12/2008 | Laufer et al. |
| 2009/0054805 A1 | 2/2009 | Boyle, Jr. |
| 2009/0076491 A1 | 3/2009 | Roschak et al. |
| 2009/0124883 A1 | 5/2009 | Wibowo et al. |
| 2009/0131765 A1 | 5/2009 | Roschak et al. |
| 2009/0143678 A1 | 6/2009 | Keast et al. |
| 2009/0204005 A1 | 8/2009 | Keast et al. |
| 2009/0275840 A1 | 11/2009 | Roschak et al. |
| 2009/0287087 A1 | 11/2009 | Gwerder et al. |
| 2009/0318904 A9 | 12/2009 | Cooper et al. |
| 2010/0041949 A1 | 2/2010 | Tolkowsky |
| 2010/0268316 A1 | 10/2010 | Brenneman et al. |
| 2010/0305463 A1 | 12/2010 | Macklem et al. |
| 2010/0312141 A1 | 12/2010 | Keast et al. |
| 2011/0082456 A1 | 4/2011 | Welt et al. |
| 2011/0146673 A1 | 6/2011 | Keast et al. |
| 2011/0146674 A1 | 6/2011 | Roschak |
| 2011/0251592 A1 | 10/2011 | Biggs et al. |
| 2011/0306997 A9 | 12/2011 | Roshak et al. |
| 2012/0085346 A9 | 4/2012 | Roschak |
| 2012/0089116 A9 | 4/2012 | Roschak |
| 2012/0123264 A9 | 5/2012 | Keast et al. |
| 2012/0221013 A1* | 8/2012 | Hawkins et al. .............. 606/128 |
| 2012/0232523 A1 | 9/2012 | Roschak |
| 2012/0289776 A1 | 11/2012 | Keast et al. |
| 2012/0289815 A1 | 11/2012 | Keast et al. |
| 2013/0041373 A1 | 2/2013 | Laufer |
| 2013/0046198 A1 | 2/2013 | Roschak et al. |
| 2013/0046296 A1 | 2/2013 | Laufer |
| 2013/0123638 A1 | 5/2013 | Tom et al. |
| 2013/0123826 A1 | 5/2013 | Kramer et al. |

FOREIGN PATENT DOCUMENTS

| | | |
|---|---|---|
| EP | 0443256 A1 | 8/1991 |
| EP | 1151729 A1 | 11/2001 |
| EP | 1400204 A1 | 3/2004 |
| EP | 1436022 A2 | 7/2004 |
| EP | 1485033 A2 | 12/2004 |
| EP | 1485035 A2 | 12/2004 |
| EP | 1509168 A2 | 3/2005 |
| EP | 1648283 A2 | 4/2006 |
| EP | 1648284 A2 | 4/2006 |
| EP | 1786499 A2 | 5/2007 |
| EP | 1802365 A2 | 7/2007 |
| JP | 2001-104315 | 4/1989 |
| JP | 2000-107178 | 4/2000 |
| WO | WO 87/05739 | 9/1987 |
| WO | WO 89/06515 | 7/1989 |
| WO | WO 90/01300 | 2/1990 |
| WO | WO 91/08706 | 6/1991 |
| WO | WO 95/02361 | 1/1995 |
| WO | WO 95/32011 | 11/1995 |
| WO | WO 96/25886 | 8/1996 |
| WO | WO 96/39914 | 12/1996 |
| WO | WO 97/17014 | 5/1997 |
| WO | WO 97/17105 | 5/1997 |
| WO | WO 98/16161 | 4/1998 |
| WO | WO 98/28035 | 7/1998 |
| WO | WO 98/48706 | 11/1998 |
| WO | WO 98/57590 | 12/1998 |
| WO | WO 99/01076 | 1/1999 |
| WO | WO 99/11182 | 3/1999 |
| WO | WO 99/25419 | 5/1999 |
| WO | WO 99/38454 | 8/1999 |
| WO | WO 99/60953 | 12/1999 |
| WO | WO 00/21461 | 4/2000 |
| WO | WO 00/27310 | 5/2000 |
| WO | WO 00/27313 | 5/2000 |
| WO | WO 00/45742 | 8/2000 |
| WO | WO 00/67825 | 11/2000 |
| WO | WO 00/72908 | 12/2000 |
| WO | WO 00/74579 | 12/2000 |
| WO | WO 01/10314 | 2/2001 |
| WO | WO 01/13839 | 3/2001 |
| WO | WO 01/28433 | 4/2001 |
| WO | WO 01/32088 | 5/2001 |
| WO | WO 01/39672 | 6/2001 |
| WO | WO 01/49213 | 7/2001 |
| WO | WO 01/54585 | 8/2001 |
| WO | WO 01/70117 | 9/2001 |
| WO | WO 01/74274 | 10/2001 |
| WO | WO 01/89366 | 11/2001 |
| WO | WO 02/00278 | 1/2002 |
| WO | WO 02/064045 | 8/2002 |
| WO | WO 02/064190 | 8/2002 |
| WO | WO 02/069823 | 9/2002 |
| WO | WO 03/020338 | 3/2003 |
| WO | WO 03/071924 | 9/2003 |
| WO | WO 03/073358 | 9/2003 |
| WO | WO 03/088820 | 10/2003 |
| WO | WO 03/097153 | 11/2003 |
| WO | WO 03/103479 | 12/2003 |
| WO | WO 2005/006963 | 1/2005 |
| WO | WO 2005/006964 | 1/2005 |
| WO | WO 2006/014731 | 2/2006 |
| WO | WO 2006/014732 | 2/2006 |
| WO | WO 2006/130821 | 12/2006 |
| WO | WO 2006/130873 | 12/2006 |
| WO | WO 2007/033379 | 3/2007 |

(56) References Cited

FOREIGN PATENT DOCUMENTS

| WO | WO 2007/062406 | 5/2007 |
|---|---|---|
| WO | WO 2008/063935 | 5/2008 |
| WO | WO 2008/109760 | 9/2008 |

OTHER PUBLICATIONS

Choong, C., et al., "Prolongaton of patency of airway bypass stents with use of drug-eluting stents," *J. Thorac. Cardiovasc. Surg.*, 131: 60-64, 2006.

Cordis Johnson & Johnson Gateway LLC: Bx Velocity Stent. Viewed at: http://www.jnjgateway.com/home.jhtm?loc=USENG &page=viewContent&contentId=fc0de00100001015 &parentId=fcde00100001015&specialty=Circulatory_Disease_ Management&category=Cardiac_Diagnosis_Interventions &subcategory=Stents_Balloon_Expandable Viewed on Sep. 5, 2002, 4 pages (please note p. 4 of 4 is blank).

Fessler, H., "Collateral Ventilation, the Bane of Bronchoscopic Volume Reduction," *Am J. Respir Crit. Care Med.* (editorial), 171:423-425, 2005.

Flenley, D., et al., "Factors Affecting Gas Exchange by Collateral Ventilation in the Dog," *Respiration Physiology*, 15:52-69, 1972.

Hogg, W., et al., "Gas Diffusion Across Collateral Channels," *Journal of Applied Physiology*, 33(5):568-575.

Lausberg, H., et al., "Bronchial fenestraton improves expiratory flow in emphysematous human lungs," Ann. Thorac. Surg., 75:393-398, 2003.

Macklem, P., "Collateral ventilation," *N. Engl. J. Med.*, 298(1):49-50, 1978.

Menkes, H., et al., "Influence of Surface Forces on Collateral Ventilation," *Journal of Applied Physiology*, 31(4):544-549, 1971.

Panettieri, R., "Chronic Obstructive Pulmonary Disease," *Lippincott's Pathophysiology Series: Pulmonary Pathophysiology*, pp. 93-107, Grippi, M., et al., eds., J.B. Lippincott Company, Philadelphia, PA, 1995.

Pulmonary and Critical Care Medicine. Interventional Bronchoscopy with Stent Implant: Stents. Viewed at: http://view.vcu.edu/pulm-ccm/stents.htm Viewed on Aug. 26, 2002. 2 pages.

Rendina, E., et al., "Feasibility and safety of the airway bypass procedure for patients with emphysema," *J. Thorac. Cardiovasc. Surg.*, 125:1294-1299, 2003.

Terry, P., et al., "Collateral Ventilation in Man," *The New England Journal of Medicine*, 298(1):10-15, 1978.

Wagner, E., et al., "Direct Assessment of Small Airways Reactivity in Human Subjects," *Am. J. Respir. Crit. Care Med.*, 157:447-452, 1998.

Woolcock, A., et al., "Mechanical Factors Influencing Collateral Ventilation in Human, Dog and Pig Lungs," *Journal of Applied Physiology*, 30(1):99-115, 1971.

Morrell et al., "Collateral ventilation and gas exchange in emphysema", Am J Respir Crit Care Med; (3); Sep. 1994: pp. 635-641.

* cited by examiner

METHODS AND DEVICES FOR ABLATION OF TISSUE

CROSS-REFERENCE TO RELATED APPLICATIONS

The present application claims priority to U.S. Provisional Application Ser. No. 61/486,206 filed May 13, 2011 and U.S. Provisional Application No. 61/485,621 filed May 13, 2011; and is a continuation-in-part of U.S. application Ser. No. 13/107,720 filed May 13, 2011 and U.S. application Ser. No. 13/107,759 filed May 13, 2011, the contents of each of which are incorporated herein by reference in their entirety.

FIELD OF THE INVENTION

This application is directed to methods and devices for ablating tissue. The procedures described herein may be performed in various regions of the body.

BACKGROUND

Procedures have involved the insertion of an electrode directly into tumors, with a ground electrode positioned elsewhere on a patient or utilizing a bipolar electrode array. RF is sent through the electrode to generate heat in the tumor in an attempt to kill the tumor. The problem with these procedures is that generating heat around an electrode within a tumor may cause the tumor to desiccate. This increases impedance within the tumor and reduces current flow such that there isn't enough current flow to heat through and destroy the entire tumor. Multiple electrodes have been inserted into a tumor and the electrodes have been multiplexed in an attempt to energize each electrode and generate heat, however, this has shown to be complex and not very effective.

Therefore, there remains a need for a more effective and efficient apparatus and method for ablating tissue in a minimally invasive manner.

SUMMARY

Various apparatus and methods for ablating tissue are described therein.

In certain variations, a method for ablating tissue may include one or more of the following steps. One or more electrodes, e.g., a first electrode and a second electrode, may be advanced to or near a target tissue in a subject. The electrodes may be energized such that the electrodes create a plasma arc. The plasma arc generates heat which desiccates or ablates the target tissue.

An apparatus for ablating tissue may include an elongate instrument, e.g., a tube or rod. One or more electrodes, e.g., a first electrode and a second electrode, may be positioned in the elongate instrument, e.g., within channels, lumensor bores in the elongate instrument. The electrodes may be energized such that the electrodes create a plasma arc for generating heat to desiccate or ablate a target tissue.

In certain variations, various ablation methods and apparatus described herein may be guided to or near a target tissue or may access a target tissue or tumor by being advanced into and through an airway, through an opening or extra-anatomic opening created in an airway wall and to or near the target tissue or tumor beyond, at, outside or near the created opening. In other variations, the methods and apparatus described herein may be utilized to perform ablation procedures in various regions of the body utilizing various access techniques.

This application is also related to the following applications 61/485,621, filed on May 13, 2011; Ser. No. 13/107,720, filed on May 13, 2011; Ser. No. 13/107,759, filed on May 13, 2011; 61/563,369 filed Nov. 23, 2011; Ser. No. 11/538,950 filed Oct. 5, 2006; Ser. No. 12/939,968 filed Nov. 4, 2010; Ser. No. 12/939,961 filed Nov. 4, 2010; Ser. No. 12/939,956 filed Nov. 4, 2010 and the patent application filed on the same day as the present application and titled "METHODS AND DEVICES FOR EXCISION OF TISSUE"; the contents of each of which are incorporated herein by reference in their entirety.

DETAILED DESCRIPTION

Various apparatus and methods for ablating tissue in a subject are described herein. Ablation may be performed on various types of tissues in various regions of the body, including, e.g., the lung. Various types of tissue may be ablated, including, e.g., diseased tissue or tumors. In certain variations, ablation may be performed on blood vessels supplying blood to a tumor or other diseased or cancerous tissue. In certain variations, the procedures described herein may be performed through an opening, port or channel through an airway wall.

An apparatus for ablating tissue may include a heat source. The heat source may generate heat or heated steam to ablate a target tissue. A method for ablating tissue may include advancing a heat source to, near or in the proximity of a target tissue. The heat source may be left in position, next to or inside the target tissue where the heat source generates heat which desiccates, ablates, chars, vaporizes, and/or destroys the target tissue.

Various heat sources may be utilized to ablate tissue. In one variation, an apparatus for ablating tissue may include one or more electrodes. For example, on apparatus may include two electrodes. The distal ends of the electrodes may be spaced apart such that when the electrodes are energized, a plasma or a plasma arc may be formed across the gap or space between the electrodes, creating or generating heat or steam for ablating tissue. The electrodes may be energized to generate heat to desiccate or kill target tissue and/or the blood vessels supplying blood to such tissue. The electrodes may be positioned within or may extend from an elongate instrument, such as a tube, shaft or other device.

Figure 1:
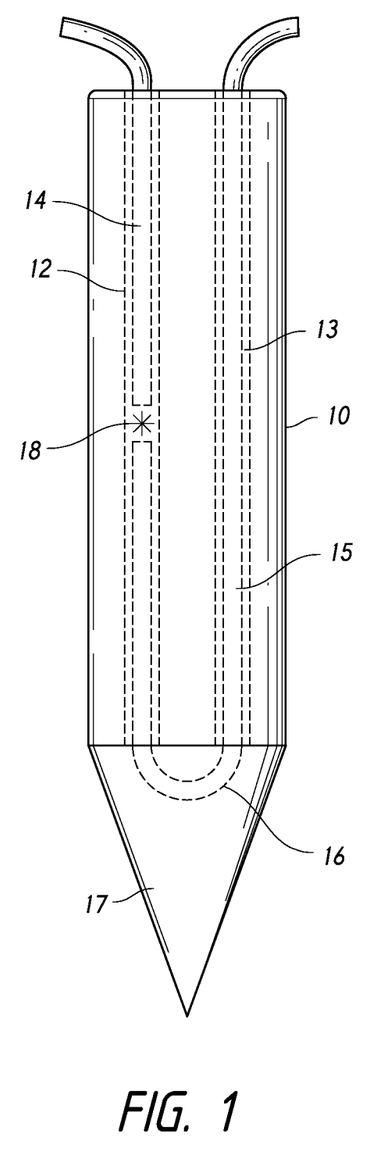
FIG. 1 illustrates a variation of an apparatus for ablating tissue.
Figure 2:
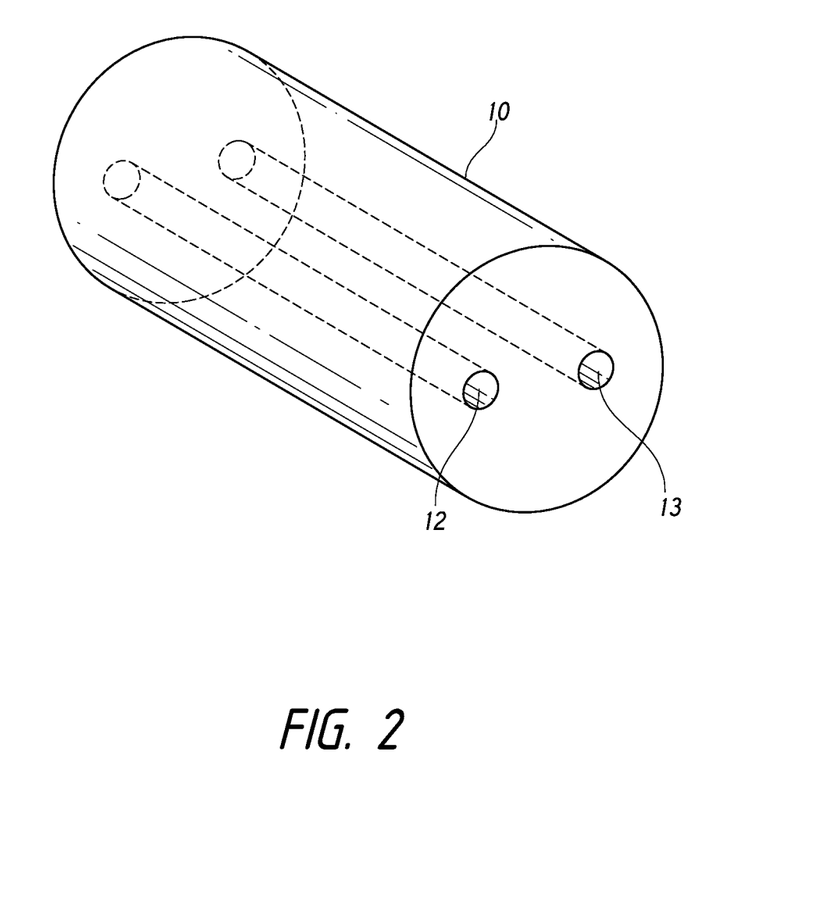
FIG. 2 illustrates a cross section of a variation of an elongate instrument of an apparatus for ablating tissue.

FIG. 1 shows one variation of an apparatus for ablating tissue. The apparatus may include an elongate instrument 10, e.g., a rod, tube shaft or sheath. The elongate instrument 10 may include one or more lumens, bores or channels. For example, the elongate instrument 10 may include a first channel 12 and a second channel 13 for holding or enclosing one more electrodes (e.g., as shown in FIG. 2). A first electrode 14 may be positioned in the first channel 12 and a second electrode 15 may be positioned in the second channel 13. The distal ends (or other portion) of the first and second electrodes 14, 15 may be spaced apart such that when the electrodes are energized an electrical arc, plasma (ionized gas), or a plasma arc 18 may be formed between the electrodes, across the gap or space between the electrodes, creating or generating heat for ablating, desiccating, and/or killing tissue. The heat or plasma may create temperatures ranging from about 1000 to about 6000 degrees C. or about 1500 to about 2000 degrees C. A heated steam may be created between the electrodes and the heated steam may coil, flow, expand or spread out and ablate and kill the target tissue. The electrodes or wires may be connected to a generator (e.g., a radiofrequency (RF) generator) as a source of energy, e.g., high frequency energy or electricity. The plasma or plasma arc may be bright.

As shown in FIG. 1, second electrode 15 may extend along a longitudinal axis of the elongate instrument 10. Second electrode 15 may also include an arc 16 or turn, positioned at the distal end of the elongate instrument 10. The arc 16 may extend into a cap 17 or tip of the elongate instrument 10. The cap 17 or tip may be pointed or cone shaped and may include a conductive material. The energized second electrode 15 may transmit energy, e.g., heat or electrical current, through the conductive cap 17, to create a cutter or cutting element. For example, the energized conductive cap 17 may be used to cut or create an opening through an airway wall and/or to cut through parenchyma or lung tissue when the conductive cap 17 is advanced through an airway wall and/or into parenchyma or lung tissue to access a target tissue. Optionally, at least a portion of second electrode 15 may extend into a first channel 12 as well.

The elongate instrument 10 may be in the form of a tube or cylinder made from glass, quartz, ceramic, or similar material or any material having a high melting point, able to withstand high temperatures. The tube or cylinder may include one or more channels, lumens or bores. One or more electrodes or wires may be positioned in the channels, lumens or bores of the tube or cylinder or otherwise within the elongate instrument. The electrodes may include a variety of materials. For example, tungsten, molybdenum, carbon, stainless steel or any other materials having similar properties or materials having a high melting point. The electrodes may have a variety of shapes or configurations, e.g., having straight or curved portions. The electrodes may be positioned in a channel that is either open to air or sealed. If sealed, the channel could be in a vacuum or filled with an inert gas. Alternatively, the channel may be melted around the electrodes, leaving no space at all. In certain variations, an elongate instrument, a tube or cylinder may encapsulate the electrodes and trap any released vapor or gas emitted from the electrodes, e.g., tungsten vapor, to prevent or reduce the emission of vapor or gas into a patient's body. In certain variations, an elongate instrument may be with or without channels.

The apparatus or electrodes for ablating tissue may be monopolar or bipolar. For example, in certain variations, a ground plate or ground electrode may be utilized. The electrodes or wires may be affixed or melted to the elongate instrument to prevent the electrode wires from moving within the elongate instrument. For example, a laser welder may be used to administer heat through a glass tube to melt the electrodes or wires to the glass tube.

In certain variations, an apparatus for ablating tissue may include one or more electrodes or conductive wires or elements for generating heat between the electrodes or wires, and/or creating plasma or a plasma arc between the electrodes, to heat and ablate tissue. The electrodes or wires may or may not be encapsulated or positioned within an elongate instrument, e.g., a tube or cylinder. In certain variations, the electrodes may extend outside of an elongate instrument to form plasma or otherwise generate heat outside of the elongate instrument. Optionally, the ends of electrodes utilized herein may be melted or shaped to provide an anode or cathode configuration. For this, each tip must be electrified and there may be no grounding plate. The grounding plate could be utilized for cutting a tract or path if the conductive wire or element most distal is one electrode and the grounding plate is the other electrode.

In one variation, a method for ablating a target tissue, e.g., a tumor, (lung or other), tissue surrounding a tumor, or blood vessels supplying blood to a tumor, may include one or more of the following steps. The elongate instrument may be navigated within the subject. For example, in the lung, the elongate instrument may be advanced within a lumen of an airway in the lung. The elongate instrument may be advanced to, near or in proximity to the target tissue. One or more electrodes positioned within the elongate instrument may be energized and may transmit energy, e.g., heat or electrical current, through a conductive distal portion or cap of the elongate instrument, providing a cutting or piercing member or tip for cutting or piercing through tissue. For example, for procedures in the lung, the energized distal portion or cap may be advanced through an airway wall, creating an opening or port through the airway wall and/or through or into the parenchyma or lung tissue. Alternately, a non-energy based tunneling device, such as a blunt dissection probe navigation and access system as described below and in U.S. patent applications: U.S. Pat. Application 61/485,621, filed on May 13, 2011; Ser. No. 13/107,720, filed on May 13, 2011; Ser. No. 13/107,759, filed on May 13, 2011; and 61/563,369 filed Nov. 23, 2011, the contents of each of which are incorporated herein by reference in their entirety, may be employed to create the opening in the airway wall and/or the tunnel to access the target tissue.

The elongate instrument and electrodes positioned therein may be advanced next to or near the target tissue or tumor or into the target tissue or tumor. The electrodes are energized (e.g., an electrical current flows through the electrode) such that a plasma or plasma arc is created between the electrodes. The electrodes and/or the plasma may generate heat to desiccate and kill the target tissue, e.g., the tumor or the blood vessels surrounding a target tissue or tumor, thereby cutting off the blood supply to the tumor. Ablation may be performed around the tumor to cut off its blood supply, e.g., in a couple of places around the tumor or all around the tumor. A crater may be ablated around the target tissue or tumor to kill the target tissue. A heated steam may be created between the electrodes and the heated steam may coil or spread out and ablate and kill the target tissue. The elongate instrument and energized electrodes are allowed to remain in place within or near the target tissue for a certain time interval or until ablation of the target tissue is achieved. Indeed, the elongate instrument and electrodes may be positioned in or near the target tissue for an amount of time sufficient to allow heat to radiate from the electrodes and/or plasma arc, and through the tissue to desiccate, ablate vaporize and/or kill the target tissue. Radiation of heat through the target tissue may improve or increase as the tissue desiccates.

In one variation, the plasma arc may remain activated and may deliver heat to the target tissue for about 0 to 5 minutes. In certain variations, the plasma arc between the electrodes may generate heat until the electrodes are burned off and the plasma arc dissipates. The apparatus may then be disposed. In certain variations, the electricity provided to the electrodes may be pulsed to avoid burning off the electrodes or to cool the electrodes such that the electrodes may last for a longer duration. In certain variations a fluid or gas may be circulated, e.g., on, in or around the elongate instrument, to provide active cooling of the electrodes.

Various imaging technologies (e.g. MRI, CT, PET, fluoroscopy, etc) may be utilized to monitor the shrinkage of a tumor or target tissue as the tumor or other target tissue or the blood vessels supplying blood to the tumor are ablated using the apparatus and/or methods described herein. Alternatively, the light generated by the electrodes and/or the plasma or plasma arc may provide feedback, e.g. rapid feedback, regarding the location of the apparatus or the electrodes and plasma arc in the patient, e.g., when using visualization technology. The light may also be visible through the patient's skin, e.g., through the chest wall when the apparatus is positioned in the lung, allowing for localization of the apparatus by transillumination or direct visualization feedback.

In certain variations, the apparatus and methods described herein may be utilized in a region of the patient's body where one or more or multiple tumors are present. For example, tumors present in an upper lobe, lower lobe, and/or right or left side of a lung may be ablated using the apparatus and methods described herein. The apparatus may be advanced into tissue of a lung via an opening created through an airway wall, where the apparatus may be used to ablate multiple tumors and/or their corresponding blood vessels while the apparatus is positioned within the lung. The tumors or nodules may each be ablated, cooked or killed, e.g., in seconds to a minute or minutes, allowing multiple tumors or nodules to be ablated in a relatively short period of time. The apparatus and methods described herein may be used for performing ablation in various regions of a patient's body, e.g., the lung, liver, and/or brain.

The energized electrodes or the plasma may create a vapor, e.g., a tungsten vapor when tungsten electrodes are utilized. Various devices for encapsulating the vapor such that the vapor is not released into a patient's body are provided. As described supra, the electrodes and plasma may be encapsulated within an elongate instrument, e.g., a glass tube (quartz glass or regular glass), which has a space for capturing the tungsten vapor. The glass tube may have dual channels in which electrodes may be positioned. The vapor may be captured within a channel and/or in a separate space or pocket within the elongate instrument or glass tube.

In one variation, a glass tube is provided for encapsulating one or more electrodes or microelectrodes. The glass tube may have a diameter ranging from about 1.0 to about 2.0 millimeters, e.g., about 1.4 millimeters. The glass tube includes one or more channels or bores having a diameter similar in size or slightly larger than the size of the electrode or wire (e.g., tungsten) to be positioned therein and an outside diameter having a size sufficient to allow the apparatus to be fed down the working channel of common endoscopes or bronchoscopes.

In one variation, a method for creating a dual channel glass (or similar material) tube for encapsulating energized tungsten electrodes and the resulting tungsten vapor includes one or more of the following steps. A glass tube is heated such that the glass may melt around one or more tungsten electrodes. A balloon (e.g., a nylon balloon) may be positioned between the electrodes, and may remain in between the electrodes as the glass is melted around the electrodes and the balloon, creating a bubble between the electrodes. Once the melting is complete and the tube having tungsten electrodes secured therein is complete, the electrodes may be energized or activated, burning away the balloon which leaves a space between the electrodes that was previously occupied by the balloon. The energized electrodes create a plasma or plasma arc across that space. The glass tube surrounds, encapsulates or encloses the electrodes and the plasma arc and may capture any released gasses or vapor, e.g., tungsten vapor. Tubes for encapsulated other types of electrodes and their resulting vapor may also be created in accordance with the above manner.

Electrodes encapsulated or enclosed in a glass tube or other elongate instrument may not oxidize or may experience minimal oxidation, allowing the electrodes to remain energized and/or burn for an extended amount of time, avoiding a rapid burn off. The encapsulated electrodes have strong conduction and generate heat sufficient for ablating tissue. Over time, the heat may melt the tube, and once the tube is melted around and/or between the electrodes to a point where the plasma arc and/or electrical arc and/or heat or heated steam is no longer generated, the apparatus may be disposed. In other variations, an elongate instrument or glass tube may be reusable where the electrodes may be replaced after use with new electrodes.

In another variation, a tungsten wire may be bonded to molybdenum either mechanically or by laser welding and a glass tube may be melted and/or bonded to the molybdenum for a stronger or improved bonding or connection between the glass and the electrodes. During melting of the glass, air/inert gas can be blown into the center of the glass tube or the formed pocket may later be filled with argon or other material. The tungsten can also be released, marking the area with a radio-opaque and MRI visible material.

In any of the above variations, a nose cone or cap of various configurations or pointed tip may be fused or attached to the distal end of the elongate instrument over an electrode. This provides a cover or distal end to the apparatus or elongate instrument, which may have a variety of shapes or configurations depending on the particular use. The cap may conduct energy (e.g., electricity or heat) and act as a piercing member or cutter. Alternatively or in addition, the cap may have sharpened or pointed end to allow for mechanical piercing or cutting.

In certain variations, glass utilized in any of the apparatus described herein may be metallized by inserting metal particles in the glass. Optionally, a sheath (e.g., a metal sheath) may be positioned around a glass tube, which provides a differing profile for temperature or delivery. For example, a thick metal may maintain a high temperature for a longer duration.

In any of the above variations, a thermocouple or temperature gauge may be positioned in an elongate instrument, e.g., in a channel or bore within the elongate instrument. The thermocouple or temperature gauge may measure the temperature of the tissue and provide feedback regarding whether or not the ablation treatment is completed or not. In certain variations, a table may be utilized which provides parameters for how long tissue should be heated based on the size of a tumor or target tissue mass and/or distance of the device from the tumor. An MRI signature may also be used to determine the temperature of the tissue as it is heated.

In certain variations, a reflector may be utilized to direct heat in a certain direction. For example, a metalized reflector may be positioned on one side of the apparatus such that all of the heat is directed to the opposite side of the apparatus. In certain variations, the elongate instrument may be parabolic and/or radiopaque to facilitate proper orientation of the elongate instrument and the electrodes during use.

The various ablating apparatus described herein, may be guided or navigated to the target tissue or tumor and/or the target tissue or tumor May be located using one or more imaging technologies, such as, x-ray, CT, MRI, fluoroscopy In certain variations, various ablation methods and apparatus described herein may be guided to or may access a target tissue or tumor by being advanced into and through an airway, through an opening or extra-anatomic opening created in an airway wall and to the target tissue or tumor beyond, at or near the created opening, where the target tissue is located in the lung, outside the lung or in another area of the body.

In certain variations, methods or platforms for accessing target tissues (e.g., diseased tissue, tumors, parenchyma or other tissues or structures) in a lung or other area of the body, through an opening, extra-anatomic opening or port through the airway wall may be utilized to access a target tissue with any of the ablation apparatus or methods described herein. The target tissue may be located outside of the airway in which the opening is created or beyond the airway wall, e.g., in the parenchyma of the lung.

Access to the central airways may be achieved by using a standard bronchoscope or other scope or elongate instrument. A target site or point in a larger airway or central airway or smaller airway may be determined or selected, which may allow a straight or substantially straight tunnel, channel or path to be created leading directly to the target tissue. Once the target site on the airway wall is located an opening is created through the airway wall at the target site on the wall by advancing a piercing member or needle to the target site and through the airway wall at the target site. The created opening may be dilated with a balloon catheter or other expandable device.

Once the opening has been dilated, a sheath or other elongate instrument may be fed through the hole or opening and into the lung tissue. The sheath may contain a dissecting catheter and the tip of the dissecting catheter may be sharp to tunnel through tissue or it may be blunt or rounded to allow it to tunnel without perforating blood vessels or other structures. The tip may tunnel or advance through the lung tissue in a substantially straight path where turns are minimized or eliminated. Once the sheath and dissecting catheter are fed to or near the target tissue or tumor, the dissecting catheter may be removed, with the sheath remaining in position to be used to access the target tissue or tumor and to deliver any of the various ablation apparatus described herein to or near the target tissue or tumor to perform ablation. Various imaging techniques may be utilized to guide the bronchoscope and piercing member and to guide the sheath, dissecting catheter, and/or ablation apparatus through the airway to the target site on the airway wall and/or to the target tissue for removal. Imaging techniques may include fluoroscopy, computed tomography, positron emission technology, magnetic resonance imaging, or ultrasound.

In certain variations, the multiple steps of the above procedure, i.e., creating an opening in the airway wall, going through the opening to dilate it and/or extending an instrument or apparatus through the opening to access a target tissue for ablation, may be performed with a single device or with more than one device. For example, a multi purpose device, e.g., a variation of an ablation apparatus as described herein, may create an opening with an energized piercing tip, and be advanced through the opening to dilate the opening and/or access a target tissue to perform ablation. Alternatively, the above procedure may be performed with more than one device, e.g., utilizing separate devices to create an opening, to dilate the opening and/or access a target tissue via the created opening with an ablation apparatus (as described herein) to ablate tissue.

The various ablation methods or apparatus described herein may also be guided or navigated to or may access a target tissue or tumor using any of the various devices or methods for creating an extra-anatomic opening in an airway wall and/or accessing tissue through an extra-anatomic opening through an airway wall as described in the following: U.S. patent applications: 61/485,621, filed on May 13, 2011; Ser. No. 13/107,720, filed on May 13, 2011; Ser. No. 13/107,759, filed on May 13, 2011; 61/563,369 filed Nov. 23, 2011; Ser. No. 11/538,950 filed Oct. 5, 2006; Ser. No. 12/939,968 filed Nov. 4, 2010; Ser. No. 12/939,961 filed Nov. 4, 2010; and Ser. No. 12/939,956 filed Nov. 4, 2010; the contents of each of which are incorporated herein by reference in their entirety.

In certain variations, any of the imaging technologies described above may be incorporated into an ablation apparatus or may be performed through an elongate instrument of the apparatus such that navigation or tracking, tissue cutting, and tissue ablation may be performed by a single device or, alternatively, by multiple devices provided via the elongate instrument or other instrument.

Any of the variations described herein may used for cutting or ablating tissue in any region of the body, e.g., the lung, liver, or brain via various access points, utilizing minimally invasive or open surgery techniques.

All publications, patent applications, patents, and other references mentioned herein are incorporated by reference in their entirety. To the extent there is a conflict in a meaning of a term, or otherwise, the present application will control. Although variations of the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. It is also contemplated that combinations of the above described embodiments/variations or combinations of the specific aspects of the above described embodiments/variations are within the scope of this disclosure.

Each of the individual variations described and illustrated herein has discrete components and features which may be readily separated from or combined with the features of any of the other variations. Modifications may be made to adapt a particular situation, material, composition of matter, process, process act(s) or step(s) to the objective(s), spirit or scope of the present invention.

Methods recited herein may be carried out in any order of the recited events which is logically possible, as well as the recited order of events. Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

This disclosure is not intended to be limited to the scope of the particular forms set forth, but is intended to cover alternatives, modifications, and equivalents of the variations described herein. Further, the scope of the disclosure fully encompasses other variations that may become obvious to those skilled in the art in view of this disclosure. The scope of the present invention is limited only by the appended claims.

I claim:

1. A method for ablating tissue, the method comprising:
   advancing an instrument having a first electrode and a second electrode to or near a target tissue in a subject; and
   energizing the electrodes such that the electrodes create a plasma arc encapsulated within the instrument, wherein the plasma arc generates heat; and ablating the target tissue using the heat generated by the plasma arc.

2. The method of claim 1, wherein the plasma arc is positioned next to a tumor such that the heat desiccates or ablates blood vessels supplying blood to the tumor.

3. The method of claim 1, wherein the plasma arc generates a heated steam which desiccates and ablates the target tissue.

4. The method of claim 1, wherein the first and second electrodes are positioned within an elongate instrument, wherein the elongate instrument comprises an electrical cutting distal tip for cutting tissue to advance the electrodes to the target tissue.

5. The method of claim 1, wherein light generated by the plasma arc provides feedback regarding the localization of the plasma arc in the patient.

6. The method of claim 5, wherein the light is visible through the subject's skin, e.g., allowing for localization of the apparatus.

7. The method of claim 1, further comprising, providing imaging to monitor target tissue shrinkage.

8. The method of claim wherein the first and second electrodes are advanced through an
   opening through an airway wall to position the plasma arc next to a target tissue or tumor in the lung.

9. The method of claim 1, wherein the heat or plasma arc may create temperatures ranging
   from about 1000 to about 6000 degrees C.

10. An apparatus for ablating tissue comprising:
    an elongate instrument;
    a first electrode and a second electrode enclosed by a wall of the elongate instrument, wherein the wall of the elongate instrument enclosing the electrodes is glass, and wherein the electrodes are configured to create a plasma arc within the instrument for generating heat which is thermally conducted through the wall at the elongate instrument to the tissue to be ablated, and wherein said wall is shaped and positioned around the electrodes such that the plasma arc is captured by said elongate instrument.

11. The apparatus of claim 10, wherein the elongate instrument comprises a tube having a
    first channel and a second channel, wherein at least a portion of the first electrode is positioned within the first channel and at least a portion of the second electrode is positioned in the second channel.

12. The apparatus of claim 10, wherein the elongate instrument is configured to encapsulate vapor released from the electrodes.

13. The apparatus of claim 10, wherein the electrodes are configured to burn off after a period of time.

14. The apparatus of claim 10, wherein the electrodes are made from tungsten or molybdenum.

15. The apparatus of claim 10, wherein the elongate instrument comprises a conductive cap positioned at a distal end of the elongate instrument, wherein a portion of the second electrode is positioned within the cap, such that the cap functions as an electrical cutter.

16. The apparatus of claim 10, further comprising an imaging mechanism for guiding or
    tracking the apparatus.

17. The apparatus of claim 10, wherein light generated by the plasma arc provides feedback
    regarding the localization of the plasma arc in the patient using.

18. The apparatus of claim 10, wherein the heat or plasma may create temperatures ranging
    from about 1000 to about 6000 degrees C.

19. The apparatus of claim 10, wherein the elongate instrument is configured to be advanced
    through an opening through an airway wall to position the plasma arc next to a target tissue or tumor in a lung.

* * * * *